United States Patent
Soya et al.

(10) Patent No.: US 6,638,725 B2
(45) Date of Patent: Oct. 28, 2003

(54) METHOD FOR ASSAYING RECEPTOR BINDING PROPERTY AND REAGENT FOR THE ASSAY

(75) Inventors: Yoshihiro Soya, Tsuruga (JP); Shigeaki Nishii, Tsuruga (JP); Kazuhiro Matsui, Tsuruga (JP); Takuya Ishibashi, Tsuruga (JP); Yoshihisa Kawamura, Tsuruga (JP)

(73) Assignee: Toyo Boseki Kabushiki Kaisha, Osaka (JP)

(*) Notice: Subject to any disclaimer, the term of this patent is extended or adjusted under 35 U.S.C. 154(b) by 0 days.

(21) Appl. No.: 09/490,053

(22) Filed: Jan. 24, 2000

(65) Prior Publication Data

US 2001/0046683 A1 Nov. 29, 2001

(30) Foreign Application Priority Data

Jan. 25, 1999 (JP) .......................................... 11-015980
Jun. 21, 1999 (JP) .......................................... 11-174536

(51) Int. Cl.$^7$ ........................ G01N 33/53; G01N 33/577
(52) U.S. Cl. .................... 435/7.1; 435/6; 435/7.2; 435/7.3; 435/7.4; 435/75; 435/7.6; 435/7.7; 435/7.8; 435/7.9; 424/1.49; 436/504; 436/536; 436/538; 436/542; 530/324; 530/344; 530/350; 530/415; 530/812; 530/816; 530/827
(58) Field of Search .................. 435/6, 7.1–7.9, 435/69.7, 71.2, 91.2, 320.1, 849, 969, 973, 810; 424/1.49; 436/504, 536, 538, 542; 536/23.1, 24.1, 24.3, 24.33; 530/324, 344, 350, 415, 812, 816, 827

(56) References Cited

U.S. PATENT DOCUMENTS

| | | | |
|---|---|---|---|
| 4,292,403 A | * 9/1981 | Duermeyer | ..................... 435/5 |
| 4,410,633 A | 10/1983 | Hertl et al. | .................. 436/500 |
| 5,246,869 A | * 9/1993 | Potter et al. | ................. 436/518 |
| 5,389,517 A | * 2/1995 | Wotiz et al. | ................... 435/7.1 |
| 5,770,176 A | * 6/1998 | Nargessi | ..................... 424/1.49 |
| 5,814,461 A | * 9/1998 | Bergmann et al. | ........... 435/7.1 |
| 5,876,946 A | * 3/1999 | Burblaum et al. | ........... 435/7.1 |

FOREIGN PATENT DOCUMENTS

| | | | | |
|---|---|---|---|---|
| WO | WO 95/06258 | * 3/1995 | .......... G01N/33/74 |
| WO | WO 98/45711 | 10/1998 | .......... G01N/33/68 |

OTHER PUBLICATIONS

Garrett et al., "A nonisotopic estrogen receptor–based assay to detect estrogenic compounds.", Nat. Biotechnology (1999), 17(12), 1219–1222.*

Gross et al., "In vitro recognition of diethystilbestrol by Anti–azobenzoyl estradiol IgG.", Steroids (1970), vol. 16, No. 4.,pp. 387–391.*

Arnold et al., "A yeast estrogen screen for examining the relative exposure of cells to natural and xenoestrogens"., Environ, Health Perspect, 104, 544–549, 1996.*

A Yeast Estrogen Screen For Examining the Relative Exposure of Cells to Natural and Xenoestrogens, Steven F. Arnold et al. Environ. Health Perspect., 104: 544–549 (1996).

The E–Screen Assay as a Tool to Identify Estrogens: An Update on Estrogenic Environmental Pollutants, Ana M. Soto et al. Environ. Health Perspect., 103: 113–122 (1995).

* cited by examiner

Primary Examiner—Long V. Le
Assistant Examiner—Lisa V. Cook
(74) Attorney, Agent, or Firm—Morrison & Foerster LLP

(57) ABSTRACT

The present invention provides a method capable of simultaneous processing of plural test samples for the receptor binding property of a chemical substance, which does not require immobilization of the receptor or a special device, and a reagent to be used for this method. That is a method for assaying the receptor binding property of an assay target substance is provided, the method comprising the steps of (a) competitively reacting a known concentration of a ligand and the assay target substance with a known concentration of the receptor in a solution, (b) measuring, without physically removing the ligand bound with the receptor prior to the assay, the amount of a free ligand in the solution using one or more antibodies against the ligand, and (c) determining the receptor binding property of the assay target substance using the amount of the free ligand as an index.

6 Claims, No Drawings

METHOD FOR ASSAYING RECEPTOR BINDING PROPERTY AND REAGENT FOR THE ASSAY

This application claims priority to Japanese Patent Application Nos. 15980/1999, filed Jan. 25, 1999 and 174536/1999, filed Jun. 21, 1999, the contents of which are incorporated by reference.

TECHNICAL FIELD OF THE INVENTION

The present invention relates to a method for assaying a receptor binding substance in an aqueous sample (e.g., biological material, sea water, river water, ground water and the like), or a method for assaying the receptor binding property of a chemical substance, and an assay reagent to be used for this method.

BACKGROUND OF THE INVENTION

Recent reports have revealed that substances induce various biochemical reactions that occur in a living body. These substances bind with their receptors in the body and cause release of signal transmitters that induce such reactions. The receptors are largely divided into those present on the cell membrane and those present in a cell or nucleus.

The receptors present on the cell membrane are hormone receptors such as adrenergic receptor, luteinizing hormone receptor and the like. Many of these receptors are responsible for intracellular regulation through signal transmission and amplification via tyrosine kinase, adenylate cyclase and the like that are regulated by the interactions of the receptors and their ligands. Those present in a cell or nucleus are exemplified by estrogen receptor, retinoide receptor and the like.

Some receptors act as a carrier in blood, such as transferrin. In particular, the action mechanism of nuclear receptor is considered to involve binding of a nuclear receptor and its ligand, which activates a nucleic acid binding region of the receptor, and binding thereof with the nucleic acid to control transcription and translation from the nucleic acid, which ultimately results in the control of various reactions in the body.

The binding of substance and receptor has been investigated and studied as models representing various reactions in the body. By the receptor is meant a substance which is not an antibody and which shows hormone binding property, biochemical messenger, steroid, drug, drug metabolite, polypeptide, protein, vitamin, alkaloid, monosaccharide, disaccharide, polysaccharide and the like.

There are some methods to evaluate in vitro the receptor binding property of a substance. They include a method using a radioisotope (Obourn, J. D. et al., *Biochemistry*, 32, 6229–6236, 1993), a method using fluorescence depolarization (Bolger, R. et al., *Environ. Health Perspect.*, 106, 551–557, 1998), a method using surface plasmon resonance (Ward, L. D. et al., *J. Biol. Chem.*, 269, 23286–23289, 1994), a method using microcalorimeter for thermodynamic assay (Moore, J. L. et al., *J. Biol. Chem.*, 271, 21273–21278, 1996) and the like.

As a method in vivo, there have been reported and practiced a method using a cultured cell (Soto, A. M. et al., Environ. Health Perspect., 103, 113–122, 1995), a method using recombinant yeast (Arnold, S. F. et al., *Environ. Health Perspect.*, 104, 544–548, 1996) and the like.

The reported method using fluorescence depolarization by Bolger et al comprises competitively reacting a fluorescent-labeled tracer with a receptor and an assay target substance with a receptor, and measuring depolarization of the fluorescence due to the binding of the tracer and the receptor. This method is defective in that the use of the fluorescent-labeled tracer causes lower reactivity and the method is subject to an influence of a contaminating fluorescent substance in the sample and the cloudiness of the sample.

The method using a radioisotope by Obourn et al comprises competitively reacting an RI-labeled tracer with a receptor and an assay target substance with a receptor, and quantitatively assaying the radioisotope bound with the receptor. This method can be used only in a specific facility because it uses a radioisotope that limits facility and workability.

The method using surface plasmon resonance by Ward et al uses an immobilized receptor, and analyzes the direct molecular interaction between the assay target substance and the receptor. However, this method fails to simultaneously process plural samples, and requires an expensive sensor chip and a special apparatus.

The method for thermodynamic assay by Moore et al is superior in that it does not require immobilization of receptor or use of a labeled tracer. However, this method also fails to simultaneously process plural samples and requires a special apparatus.

In recent years, a need has arisen for a broad screening of endocrine disrupting chemical (EDC) (Toyama, C., Clinical Endocrinology, 46, 517–528, 1998), that requires examination of receptor binding property of known or new tens of thousands of chemical substances. The above-mentioned methods cannot process plural samples simultaneously, and therefore, enormous time and labor are needed. There is an urgent demand on an assay method for the interaction between a receptor and a chemical substance, that can achieve a high throughput.

SUMMARY OF THE INVENTION

It is therefore an object of the present invention to provide a method capable of simultaneous processing of plural test samples for the receptor binding property of a chemical substance, which does not require immobilization of the receptor or a special device, and a reagent to be used for this method.

The present invention is based on the finding that a ligand not bound with a receptor can be assayed alone with ease by the steps comprising competitively reacting a ligand and an assay target substance with the receptor in a solution, and, without physically removing the ligand bound with the receptor, further adding an antibody against the ligand and a labeled ligand to allow reaction.

Accordingly, the present invention provides the following.

1. A method for assaying the receptor binding property of an assay target substance, comprising the steps of
   (a) competitively reacting a known concentration of a ligand and the assay target substance with a known concentration of the receptor in a solution,
   (b) measuring, without physically removing the ligand bound with the receptor prior to the assay, the amount of a free ligand in the solution using one or more antibodies against the ligand, and
   (c) determining the receptor binding property of the assay target substance using the amount of the free ligand as an index.

2. The method of 1 above, wherein the step (b) comprises adding one or more antibodies against the ligand and a labeled ligand to the reaction mixture obtained in step (a) to allow competitive reaction of the antibody and the free or labeled ligand, and measuring the amount of the label bound or not bound with the antibody.
3. The method of 1 above, wherein the antibody retains its activity by 60% or more in a 1% organic solvent.
4. The method of 1 above, wherein the ligand is not labeled, bound, processed or denatured.
5. The method of 1 above, wherein the receptor is used in an amount that produces binding of 50% or more of the ligand with the receptor.
6. The method of 1 above, wherein the receptor is selected from the group consisting of receptors of hormone, drug, drug metabolite, polypeptide, protein, saccharides, biochemical messenger and vitamin and ligand binding domains thereof.
7. A reagent for assaying the receptor binding property of a substance, comprising a reagent containing a known concentration of a receptor, a reagent containing a known concentration of a ligand of a known concentration of the receptor, and a reagent for measuring a free ligand, which contains one or more antibodies against the ligand.
8. The reagent of 7 above, further comprising a reagent containing the ligand which has been labeled.
9. The reagent of 7 above, wherein the antibody retains its activity by 60% or more in a 1% organic solvent.
10. The reagent of 7 above, wherein the ligand is not labeled, bound, processed or denatured.
11. The reagent of 7 above, wherein the receptor is used in an amount that produces binding of 50% or more of the ligand with the receptor.
12. The reagent of 7 above, wherein the receptor is selected from the group consisting of receptors of hormone, drug, drug metabolite, polypeptide, protein, saccharides, biochemical messenger and vitamin and ligand binding domains thereof.

DETAILED DESCRIPTION OF THE INVENTION

The present invention brief relates to a method for evaluating the receptor binding property of a natural compound or artificially synthesized compound. According to this method, the substance to be evaluated and an unlabeled ligand are competitively reacted at a binding site on the receptor, and the concentration of the free ligand is directly assayed in the reaction mixture, without separating the ligand bound with the receptor from the free ligand. In the present invention, the receptor includes hormone, drug, drug metabolite, polypeptide, protein, saccharides, biochemical messenger, vitamin, ligand binding domains thereof, and the like. The receptor embraces receptors on biomembranes (e.g., luteinizing hormone receptor, follicle-stimulating hormone receptor, human choriogonadotropin receptor, thyroid-stimulating hormone receptor and the like), nuclear and cytoplasmic receptors (e.g., estrogen receptor, androgen receptor, progesterone receptor, peroxisome amplification promoting receptor, glucocorticoid receptor, retinoic acid receptor, retinoid X receptor, thyroid receptor, ubiquinone receptor, vitamin D receptor, mineral corticoid receptor and the like) and receptors in serum as carrier (e.g., thyroglobulin, transferrin and the like). Therefore, the ligand in the present invention means luteinizing hormone, follicle-stimulating hormone, human choriogonadotropin, thyroid-stimulating hormone, estrogen, androgen, progesterone, peroxisome, glucocorticoid, retinoic acid, retinoid X, thyroid, ubiquinone, vitamin D, mineral corticoid, iron and the like, which correspond to the above-mentioned receptors.

The binding ratio with the receptor of assay target substance and ligand is determined according to their existing ratios and respective binding constants. When a receptor and a ligand are present at given concentrations, the binding ratio of the ligand with the receptor becomes constant. When a substance having receptor binding property is present, however, the amount of the ligand that binds with the receptor decreases depending on the amount of the substance and its binding constant, and the amount of free ligand increases. By measuring the variation in the concentration of the ligand, indirect evaluation of the receptor binding property of a substance is enabled.

The present invention most characteristically comprises the following steps to evaluate the receptor binding property:

(a) adding a ligand known to bind with the receptor,
(b) competitively reacting an assay target substance and the ligand on a binding site of the receptor and
(c) measuring, without physically removing the ligand bound with the receptor prior to the assay, the amount of a free ligand in the reaction mixture. According to this method, unlike conventional methods, the receptor or ligand does not need to be immobilized on an insoluble carrier. In addition, since the ligand to be competitively reacted with a receptor is not labeled, the reactivity does not decrease. Moreover, the ligand may be any as long as it has receptor binding property, and an economically and efficiently assayable one can be used. The physical removal here means a step for separating a ligand bound with a receptor from a free ligand, which may be a conventional method such as washing, filtration through a filter, separation by magnetism and the like. The separation may be conducted during the assay of free ligand, for example, when a solid-phased antibody is used and the like.

The assay of an endocrine disrupting chemical has recently been highly demanded. The combination of a receptor and a ligand for screening of such substance, while the combination being subject to no particular limitation, is preferably an estrogen receptor and estradiol, estrone or estriol, a thyroid hormone receptor and thyroxine or triiodothyronine and the like. The assay method of the present invention can be used for the combination of a receptor and a ligand other than those mentioned above.

The above-mentioned ligand preferably has not undergone labeling, binding, processing or denaturing. The amount of the receptor to be added is preferably such as allows for binding of not less than 50% of the coexisting ligand. When the concentration is less than 50%, the ligand shows very small variation in the concentration, which in turn makes the evaluation of receptor binding property difficult.

The concentration of free ligand is measured by a known method. Preferably, a spectroscopical method or a fluorescence/luminescence assay is applied. When the spectroscopical method is used, the assay generally includes competitive reaction of the free ligand and an enzyme-labeled ligand with an immobilized anti-ligand antibody. The enzyme to be used as a label may be peroxidase, alkaline phosphatase, β-galactosidase, acetylcholinesterase and the like, with preference given to peroxidase. For a fluorescence/luminescence assay, a fluorescent marker, a luminescent marker and the like are used instead of an enzyme label. Examples of the fluorescent marker include fluorescein, rhodamine and the like and examples of the luminescent marker include acridinium ester, photoprotein (e.g., aequorin) and enzyme (e.g., luciferase).

The antibody to be used in the present invention is free of any particular limitation as to the origin, property and the like, as long as it can assay a ligand. The antibody may be a monoclonal antibody or a polyclonal antibody. When a substance reactive with the antibody is present in a sample, an antibody against the substance is preferably added to the reagent to obliterate an influence of the substance on the assay. Alternatively, when an antibody is immobilized on a water insoluble carrier, an antibody (secondary antibody) against the antibody to be used for higher orientation may be previously bound with a water insoluble carrier. It is also possible to use a known method for providing a solid phase, such as a method comprising previously immobilizing protein A or protein G and binding the antibody, or binding a biotinylated antibody on a water insoluble carrier on which streptavidin or avidin has been immobilized in advance.

Since the assay target substance may have lower solubility in water, an organic solvent is used to dissolve the sample. While the organic solvent to be used is not particularly limited, preferred are methanol, dimethyl sulfoxide (DMSO), acetonitrile, ethanol and the like. In this case, the antibody to be used needs to be resistant to the organic solvent to be used. Desirably, this antibody retains the antibody activity by 60% or more in an organic solvent having a 1% concentration. By the antibody activity here is meant the specific affinity thereof for the ligand to be used.

The present invention is explained in more detail in the following by way of Examples, to which the present invention is not limited.

EXAMPLE 1

Evaluation of Estrogen Receptor Binding Property

Composition of Reagent 1 estrogen receptor: 100 nM (in 10 mM phosphate buffer, 150 mM NaCl; pH 7.2)

17β estradiol: 33 nM (in 10 mM phosphate buffer, 150 mM NaCl; pH 7.2)

Composition of Reagent 2 anti-estradiol antibody-bound microtiter plate

HRP-labeled estradiol

Sample

Diethylstilbesterol (0, 3.3, 10, 33, 100, 333, 1000 ng/ml)

Assay Method

A sample (30 μl) and an estrogen receptor solution (20 μl) were mixed and 17β estradiol solution (30 μl) was added, which was followed by incubation at 37° C. for 1 hr. The solution (50 μl) was dispensed to an anti-estradiol antibody-bound microtiter plate, simultaneously with which a horseradish peroxidase (HRP)-labeled estradiol solution (50 μl) was dispensed, which was followed by incubation at 37° C. for 1 hr. The reaction mixture was removed and the plate was washed 3 times with 10 mM phosphate buffer containing 0.15 M NaCl and 0.05% Tween 20. After washing, o-phenylenediamine (OPD) solution (50 μl) was added and the mixture was incubated at 37° C. for 20 min. 1N Sulfuric acid (100 μl) was added and the absorbance at 490 nm was measured. The results are shown in Table 1.

TABLE 1

| Diethylstilbesterol concentration [ng/ml] | Absorbance |
| --- | --- |
| 0 | 2.321 |
| 3.3 | 2.220 |
| 10.0 | 1.981 |
| 33.0 | 1.553 |
| 100.0 | 1.342 |
| 333.0 | 0.984 |
| 1000.0 | 0.952 |

The absorbance decreased with increasing diethylstilbesterol concentrations. Thus, diethylstilbesterol was confirmed to be able to quantitatively show the estrogen receptor binding property.

EXAMPLE 2

Evaluation of Estrogen Receptor Binding Property

Composition of Reagent 1

Estrogen receptor: 100 nM (in 10 mM phosphate buffer, 150 mM NaCl; pH 7.2)

17βestradiol: 33 nM (in 10 mM phosphate buffer, 150 mM NaCl; pH 7.2) anti-estradiol antibody-bound microtiter plate A HRP-labeled estradiol Composition of Reagent 2

Estrogen receptor: 100 nM (in 10 mM phosphate buffer, 150 mM NaCl; pH 7.2)

17β estradiol: 33 nM (in 10 mM phosphate buffer, 150 mM NaCl; pH 7.2)

anti-estradiol antibody-bound microtiter plate B

HRP-labeled estradiol

Sample diethylstilbesterol (0,1000 ng/ml; prepared with PBS, prepared with 1% DMSO solution)

Assay Method

In the same manner as in Example 1, the assay was performed.

TABLE 2

| Solvent | Diethylstilbesterol concentration (ng/ml) | Absorbance Composition 1 | Absorbance Composition 2 |
| --- | --- | --- | --- |
| PBS | 0 | 2.34 | 2.12 |
|  | 1000 | 0.98 | 0.87 |
| 1% DMSO | 0 | 2.34 | 2.12 |
|  | 1000 | 0.98 | 1.82 |

When PBS was used as a solvent, the two kinds of antibodies did not show significant difference in the assay values. When an organic solvent was used, however, the assay values varied greatly depending on the antibodies used. That is, when an antibody that shows lower reactivity in the presence of an organic solvent is used, evaluation of the receptor binding property of an assay target substance becomes difficult due to small variation in absorbance.

This application is based on application Nos. 15980/1999 and 174536/1999 filed in Japan, the contents of which are incorporated. All publications are herein incorporated by reference to the same extent as if each individual publication was specifically described herein.

What is claimed is:

1. A method for assaying the binding of an assay target substance to a receptor, comprising:

(a) competitively reacting a ligand and the assay target substance with a receptor in a solution, wherein the concentrations of the ligand and the receptor are known and the concentration of the assay target is unknown and the ligand and the assay target substance are not the same substance, (b) measuring the amount of the free ligand in the solution using one or more antibodies against the free ligand, wherein the receptor bound ligand is not removed from the solution before a binding reaction between the free ligand and the antibodies, wherein the free ligand binds with said antibodies and the receptor-bound ligand does not, and (c) measuring the binding of the assay target substance to the receptor using the amount of free ligand as an index.

2. The method of claim 1, wherein the step (b) further comprises adding one or more antibodies against the ligand and a labeled ligand to the reaction mixture obtained in step (a) to allow competitive reaction of the antibody and the free ligand or labeled ligand, and measuring the amount of the label bound or not bound with the antibody.

3. The method of claim 1, wherein the antibody retains its activity by 60% or more in a 1% organic solvent.

4. The method of claim 1, wherein prior to step (a) the ligand is not labeled, bound, processed or denatured.

5. The method of claim 1, wherein the receptor is used in an amount that produces binding of 50% or more of the ligand with the receptor.

6. The method of claim 1, wherein the receptor is selected from the group consisting of a hormone receptor, a drug receptor, a drug metabolite receptor, a polypeptide receptor, protein, a saccharide receptor, a vitamin receptor, and ligand binding domains thereof.

* * * * *